United States Patent
Muehlhausen (10) Patent No.: US 11,614,798 B2
(45) Date of Patent: Mar. 28, 2023

(54) EYE TRACKING (71) Applicant: Tobii AB, Danderyd (SE)

(72) Inventor: Andrew Muehlhausen, Danderyd (SE)

(73) Assignee: TOBII AB, Danderyd (SE)

( * ) Notice: Subject to any disclaimer, the term of this patent is extended or adjusted under 35 U.S.C. 154(b) by 0 days.

(21) Appl. No.: 16/833,757

(22) Filed: Mar. 30, 2020

(65) Prior Publication Data
US 2021/0303062 A1 Sep. 30, 2021

(51) Int. Cl.
G06F 3/01 (2006.01)
G06F 3/04815 (2022.01)
G06F 3/04842 (2022.01)
G06V 40/19 (2022.01)

(52) U.S. Cl.
CPC .......... G06F 3/013 (2013.01); G06F 3/04815 (2013.01); G06F 3/04842 (2013.01); G06V 40/19 (2022.01)

(58) Field of Classification Search
CPC .. G06F 3/013; G06F 3/04815; G06F 3/04842; G06K 9/00604
See application file for complete search history.

(56) References Cited

U.S. PATENT DOCUMENTS 9,665,171 B1 * 5/2017 Skogo ...................... G09G 5/37
2018/0008141 A1 1/2018 Krueger
2019/0038130 A1 * 2/2019 Lawrence .............. A61B 5/036

OTHER PUBLICATIONS

Gruters, et al., "The Eardrums Move When the Eyes Move: A Multisensory Effect on the Mechanics of Hearing", Proceedings of the National Academy of Sciences, vol. 115, No. 6, Jan. 23, 2018, pp. E1309-E1318.
SE1950376-2, "Office Action", dated Oct. 17, 2019, 8 pages.

* cited by examiner

Primary Examiner — Mihir K Rayan
(74) Attorney, Agent, or Firm — Kilpatrick Townsend & Stockton LLP (57) ABSTRACT A system for determining a gaze point of a user, the system comprising at least one sensor configured to determine at least one signal representative of a variation in a volume of the interior of a user's ear, and a processor configured to determine a direction of eye movement of the user based on the determined signal, and determine a gaze point of the user based on the direction of eye movement. Further, the disclosure relates to a corresponding method.

15 Claims, 5 Drawing Sheets

EYE TRACKING

CROSS-REFERENCES TO RELATED APPLICATIONS

This application claims priority to Swedish Application No. 1950376-2, filed Mar. 27, 2019; the content of which are hereby incorporated by reference.

FIELD

The present disclosure generally relates to determining a gaze point of a user. More specifically, the present disclosure generally relates to a system and method of determining a gaze point of a user based on a variation in a volume of the interior of a user's ear.

BACKGROUND

User-apparatus interaction generally relates to the input of information to and control of an apparatus (e.g. a computer, a tablet computer, a desktop computer, a handheld device such as a mobile telephone or similar) by a user. Many popular computer programs and operating systems have been developed to function primarily with input methods involving physical contact (e.g., by means of a mouse or key board). This type of physical input method is sometimes referred to as contact-required input method. It can be difficult for people who desire to use non-contact input methods to interact with these computer programs and operating systems. For example, some users must use non-contact input methods (e.g., because of an injury or disability).

As computer technology has evolved, non-contact input methods have been developed. An example of a non-contact input device allowing for non-contact input is described in the U.S. Pat. No. 7,572,008. This United States Patent describes an eye-tracking device developed by Tobii AB, Sweden. Eye-tracking devices may operate on the principle of illuminating an eye of a user with infrared light and utilizing an image sensor to detect reflection of the light from the eye. A processor may use the data from the image sensor to calculate, or otherwise determine, the direction of the user's gaze. Non-contact input methods utilizing a point of a user's gaze are sometimes referred to as gazed-based control methods. Gaze-based control methods are generally used, or preferred, by users who have good vision.

During a rapid movement of the user's gaze (sometimes referred to as a saccade), it becomes non-trivial to accurately sense the movement and an updated point of a user's gaze, and to control an apparatus accordingly and with minimum delay. It is therefore desired to develop approaches to eye-tracking that mitigate these issues.

SUMMARY

The present disclosure provides methods and systems for determining a gaze point of a user, which uses measurements from the ear of a user to determine corresponding eye movement. It has been shown that changes to the volume of an interior of a user's ear can precede and/or accompany a saccadic eye movement. By sensing such changes in volume, the disclosed system can predict saccadic eye movements before they occur, and can accurately determine an anticipated gaze point of a user. The determination of gaze points can enable interaction between a user and an apparatus, sometimes referred to as user-apparatus interaction or human-computer interaction. More specifically, the determination of gaze points can enable gaze-based control of an apparatus, such as a computer, a tablet computer, or a desktop computer.

In accordance with an aspect of the disclosure there is provided a method of determining a gaze point of a user, the method comprising determining at least one signal representative of a variation in a volume of the interior of a user's ear, determining a direction of eye movement of the user based on the determined signal, determining a gaze point of the user based on the direction of eye movement.

Optionally, determining the signal comprises using at least one sensor disposed inside, adjacent to or outside the user's ear. Optionally, the at least one sensor comprises a microphone, a sonar device and/or a radar device. Optionally, the variation in a volume of the interior of a user's ear comprises a variation in the shape of the interior of the user's ear. Optionally, the variation in a volume of the interior of a user's ear comprises a variation in the pressure in the interior of the user's ear.

Optionally, a variation in the volume in a first sense indicates a substantially contralateral eye movement with respect to the user's ear, and a variation in the volume in a second sense, opposite to the first sense, indicates a substantially ipsilateral eye movement with respect to the user's ear.

Optionally, the method further comprises determining the direction of eye movement before the eye movement occurs, and determining an anticipated gaze point based on an initial gaze point of the user and the determined direction of eye movement. Optionally, the signal comprises a first portion corresponding to a time before the eye movement occurs, the method comprising determining the direction of eye movement based on the first portion. Optionally, the signal comprises a second portion subsequent to the first portion, the second portion indicating a variation in the opposite sense to the first portion.

Optionally, the magnitude of the variation corresponds to a magnitude of the eye movement. Optionally, determining at least one signal comprises determining a first signal representative of a variation in a volume of the interior of a user's left ear, and determining a second signal representative of a variation in a volume of the interior of a user's right ear. Optionally, the eye movement is a saccadic eye movement. Optionally, the direction of eye movement is substantially horizontal.

Optionally, the method further comprises controlling a display device based on the determined gaze point. Optionally, controlling the display device comprises modifying the use of at least one system resource by modifying a first image displayed on the display device. Optionally, modifying the first image displayed on the display device comprises causing a second image to be displayed on the display device, and the second image is different than the first image at least in an area around the determined gaze point. Optionally, the second image has increased quality compared to the first image in the area around the determined gaze point. Optionally, increased quality comprises at least one selection from a group consisting of increased resolution, increased shading quality, increased texture mapping quality, increased quality of reflection rendering, increased antialiasing, increased frame rate, and increased three-dimensional rendering quality.

In accordance with an aspect of the disclosure there is provided a system for determining a gaze point of a user, the system comprising at least one sensor configured to determine at least one signal representative of a variation in a volume of the interior of a user's ear, and a processor configured to determine a direction of eye movement of the user based on the determined signal, and determine a gaze point of the user based on the direction of eye movement.

Optionally, the at least one sensor comprises a microphone, a sonar device and/or a radar device. Optionally, the at least one sensor is disposed inside, adjacent to or outside the user's ear. Optionally, the variation in a volume of the interior of a user's ear comprises a variation in the shape of the interior of the user's ear. Optionally, the variation in a volume of the interior of a user's ear comprises a variation in the pressure in the interior of the user's ear.

Optionally, a variation in the volume in a first sense indicates a substantially contralateral eye movement with respect to the user's ear, and a variation in the volume in a second sense, opposite to the first sense, indicates a substantially ipsilateral eye movement with respect to the user's ear.

Optionally, the processor is further configured to determine the direction of eye movement before the eye movement occurs, and determine an anticipated gaze point based on an initial gaze point of the user and the determined direction of eye movement. Optionally, the signal comprises a first portion corresponding to a time before the eye movement occurs, the method comprising determining the direction of eye movement based on the first portion. Optionally, the signal comprises a second portion subsequent to the first portion, the second portion indicating a variation in the opposite sense to the first portion.

Optionally, the magnitude of the variation corresponds to a magnitude of the eye movement. Optionally, the at least one sensor comprises a first sensor configured to determine a first signal representative of a variation in a volume of the interior of a user's left ear, and a second sensor configured to determine a second signal representative of a variation in a volume of the interior of a user's right ear. Optionally, the eye movement is a saccadic eye movement. Optionally, the direction of eye movement is substantially horizontal.

Optionally, the system further comprises a display device, wherein the processor is configured to control the display device based on the determined gaze point. Optionally, the processor is configured to control the display device by modifying the use of at least one system resource, comprising modifying a first image displayed on the display device. Optionally, the processor is configured to cause a second image to be displayed on the display device, and the second image is different than the first image at least in an area around the determined gaze point. Optionally, the second image has increased quality compared to the first image in the area around the determined gaze point.

Optionally, increased quality comprises at least one selection from a group consisting of increased resolution, increased shading quality, increased texture mapping quality, increased quality of reflection rendering, increased anti-aliasing, increased frame rate, and increased three-dimensional rendering quality.

In accordance with another aspect of the disclosure there is provided a computer program comprising instructions which, when executed on at least one processor, cause the at least one processor to carry out the method. In accordance with another aspect of the disclosure there is provided a carrier containing the computer program, wherein the carrier is one of an electronic signal, optical signal, radio signal, or computer readable storage medium.

The disclosed methods and systems enable a future gaze point of a user to be predicted accurately and before any eye movement occurs. This ensures that control of an apparatus that is based on a user's gaze point can be performed accurately and with minimal delay.

BRIEF DESCRIPTION OF THE DRAWINGS

Exemplary embodiments of the disclosure shall now be described with reference to the drawings in which.

Throughout the description and the drawings, like reference numerals refer to like parts.

Specific Description

The present invention will now be described more fully hereinafter. The invention may, however, be embodied in many different forms and should not be construed as limited to the embodiments set forth herein; rather, these embodiments are provided by way of example so that this disclosure will be thorough and complete, and will fully convey the scope of the invention to those users skilled in the art.

Figure 1:
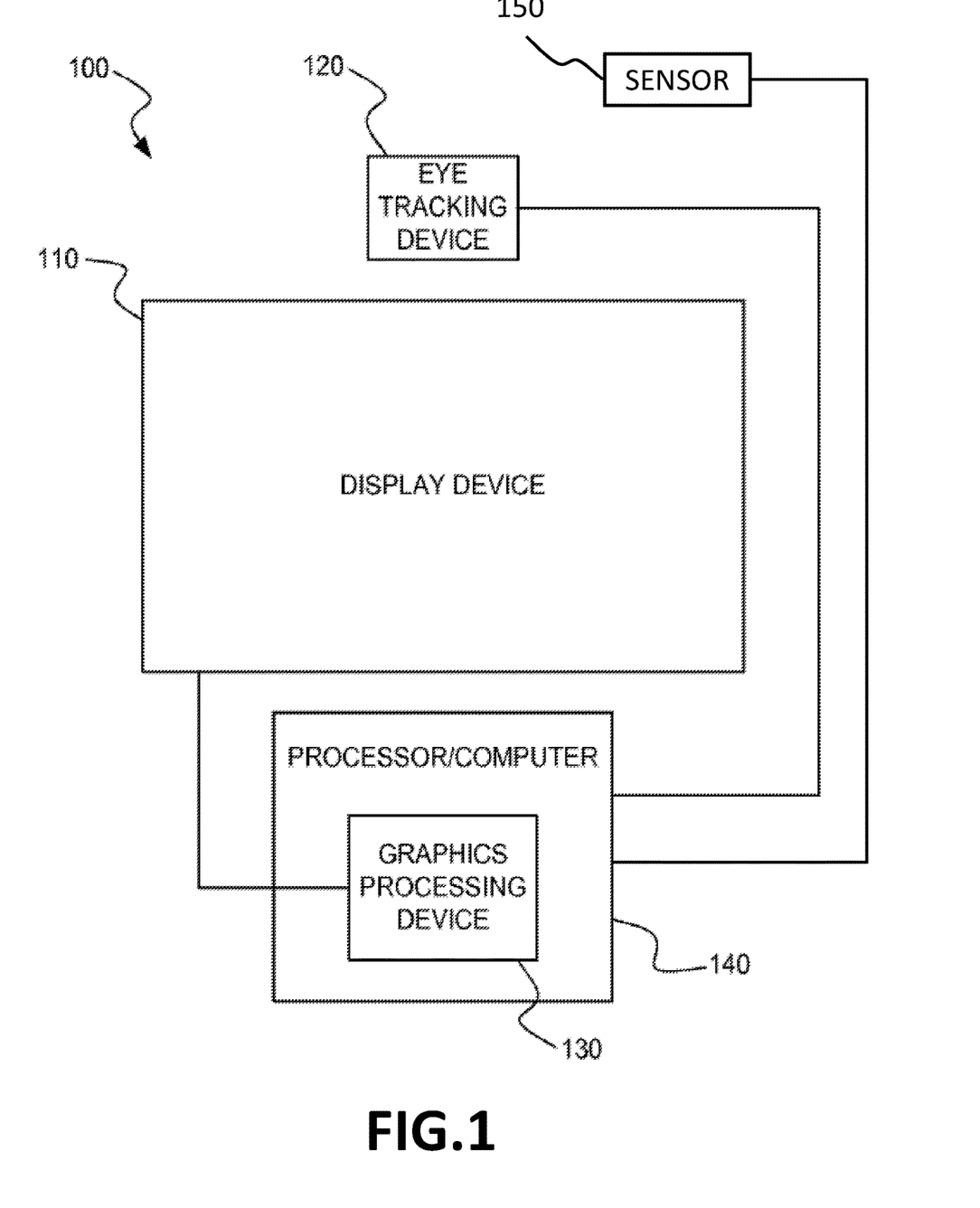
FIG. 1 illustrates a system for presenting graphics on a display device according to an embodiment.

In some embodiments of the invention, and with reference to FIG. 1, a system 100 for presenting graphics on a display device 110 is provided. The system 100 may include an eye tracking device 120 and a graphics processing device 130. In some embodiments, the system may also include a processor/computer 140, which communicates with, and controls, the graphics processing device 130. In some embodiments, any function of the graphics processing device 130 may be performed, in whole or in part, by the processor/computer 140. In some embodiments, the system may also include a sensor 150, which may monitor at least one physical characteristic of a user. The sensor may be integrated with the eye tracking device 120, or may be implemented separately. Merely by way of example, the eye tracking device 120 and/or the sensor 150 may be provided integral to, or in addition to, a personal computer 140 having the graphics processing device 130 and a central processing unit (in some configurations, the graphics processing device 130 and the central processing unit are integrated). In other embodiments, the eye tracking device 120 and/or the sensor 150 may be provided integral to, or in addition to, a gaming console or other device having the graphics processing device 130 and a central processing unit. Examples of gaming consoles include those produced and available from Microsoft™, Nintendo™, or Sony™. Thus, embodiments of the invention may be applied to the presentation of graphics in any number of possible devices and applications, including video display, video games, video production and editing, video communications, computer aided drafting and design, etc.

The eye tracking device 120 may be for determining at least one of a gaze point of a user on the display device 110, or a change in the gaze point of the user on display device 110. Eye tracking devices and methods, sometimes referred to as gaze detection systems and methods, include, for example, products produced and available from Tobii Technology AB, and which operate by using infrared illumination and an image sensor to detect reflection from the eye of a user. An example of such a gaze detection system is described in U.S. Pat. No. 7,572,008. Other alternative gaze detection systems may also be employed by the invention, regardless of the technology behind the gaze detection system. The eye tracking device 120 may employ its own processor or the processor of another device (i.e., the processor/computer 140) to interpret and process data received. When an eye tracking device is referred to herein, both possible methods of processing data are referred to.

The graphics processing device 130 employed by various embodiments of the invention may be for causing an image to be displayed on the display device 110. The graphics processing device 130 may modify what image is displayed on the display device 110 based at least in part on the gaze point of the user on the display device 110, or a change in the gaze point of the user on the display device 110, as determined by the eye tracking device 120 and/or the sensor 150. While in some embodiments a separate non-included or non-integrated display device will be controlled by the graphics processing device 130, other embodiments may include or integrate the display device 110.

The sensor 150 may be used to monitor at least one physical characteristic of a user. For example, the sensor 150 may be a pressure sensor that is used to determine the pressure the interior of a user's ear, as will be discussed in more detail below. The sensor 150 may be, for example, a microphone. The sensor 150 may equally be a sonar device or a radar device capable of detecting changes in the volume of the interior of a user's ear. Other sensors capable of sensing a change in shape of the interior of a user's ear, for example a camera, may also be used. The sensor 150 may employ its own processor or the processor of another device (i.e., the processor/computer 140) to interpret and process data received The way in which the image displayed on the display device 110 may be modified by the graphics processing device 130 may vary depending on the embodiment, but regardless, the way in which the image is displayed may be intended to increase the image quality of portions of the image on which a user's gaze, or focused gaze, is directed, relative to those portions of the image to which the user's gaze, or focused gaze, is not directed. In this manner, the use of available resources of the graphics processing device 130, and/or other system resources, are maximized to deliver image quality where it matters most on the display device 110.

Figure 2:
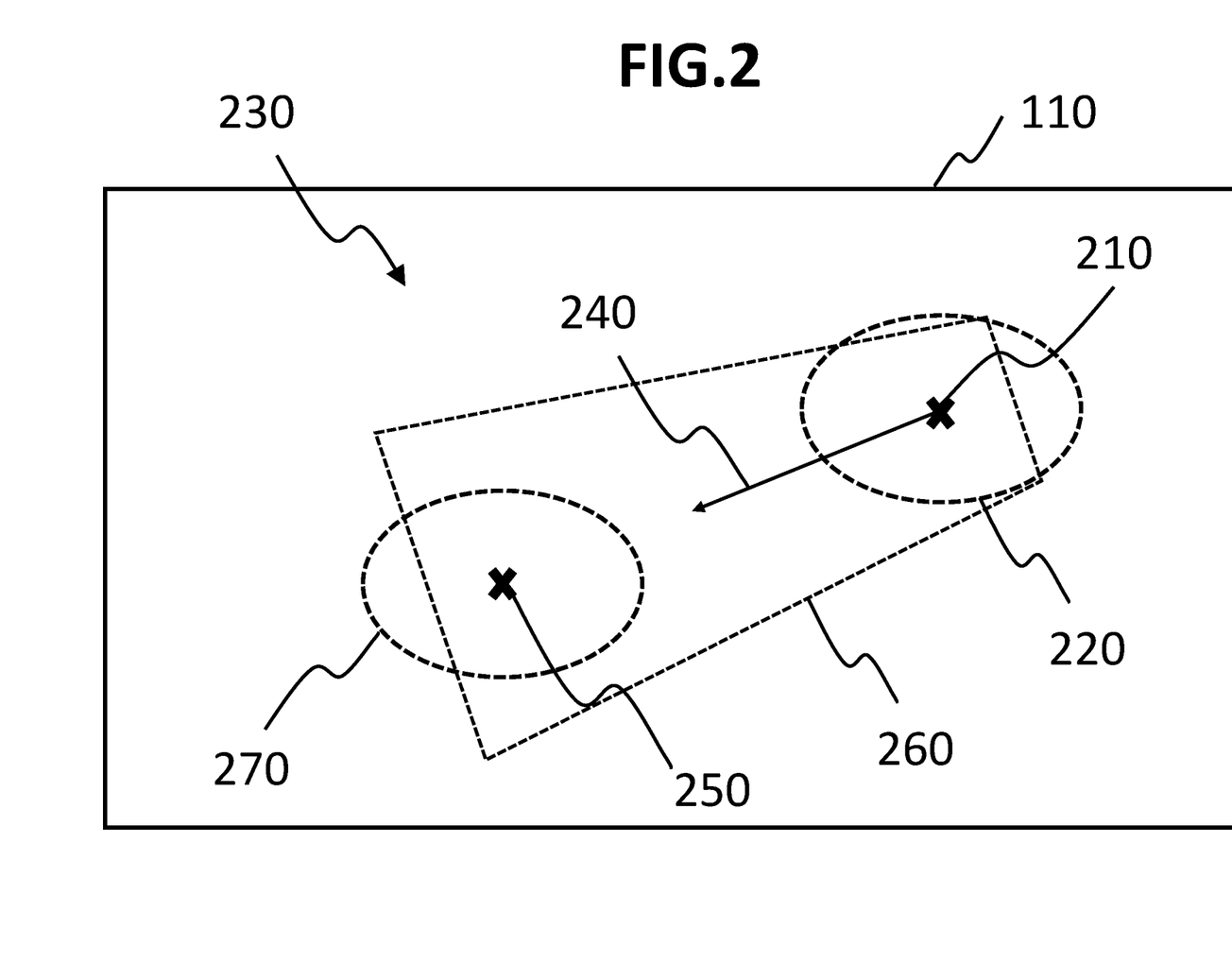
FIG. 2 illustrates a display device showing a user's gaze point and an associated eye movement.

To demonstrate, FIG. 2 illustrates a display device 110 showing a user's initial gaze point 210 and an area 220 around the user's initial gaze point 210 in which embodiments of the invention may increase the quality of the image relative to the remaining area 230 of the display device 110. Thus, in various embodiments of the invention, the quality of the image produced across the display device 110 may be increased in the area 220 around the user's initial gaze point 210 relative to a remaining area 230.

When a user saccade, represented by an arrow describing a direction of movement 240, is detected by eye tracking device 120, the size and shape of the area 220 around the user's initial gaze point 210 may change to accommodate both the initial gaze point 210 and an anticipated gaze point 250. A changed area 260, being triangular and/or trapezoidal in this embodiment, may be shaped and sized differently in other embodiments. Merely by way of example, an entire side of the display device 110 from the initial gaze point to the edges of the display in the direction of the saccade may also be included in the changed area 260 to account for more possibilities of where the user's gaze point may end. In other embodiments, a circular, oval, or square changed area 260 may be provided. In yet other embodiments, the changed area 260 may include separate and distinct areas around the initial gaze point 210 and the anticipated gaze point 270, for example an area 270 around the user's anticipated gaze point 270.

Detection of a change in the gaze point may occur in a number of fashions. As discussed above, eye-tracking devices may operate on the principle of illuminating an eye of a user with infrared light and utilizing an image sensor to detect reflection of the light from the eye. A processor may use the data from the image sensor to calculate, or otherwise determine, the direction of the user's gaze. The present disclosure uses secondary means to detect a change in the gaze point, which allows a faster and more accurate determination.

Specifically, it has been shown that the eardrums of a user move with saccadic eye movements. As such, measurements of the interior ear of a user can be used to detect eye movements. The eardrum motion is oscillatory and begins before saccade onset. The amplitude and phase of the oscillations depends on the direction and amplitude of the saccade. As such, the direction and magnitude of an eye movement can be determined from a measurement of the interior ear of a user. For example, the sensor 150 may be used to monitor the interior of a user's ear in order to detect such movement of the eardrum. A signal from the sensor 150 may then be used to determine the direction and magnitude of an eye movement of the user.

Figure 3:
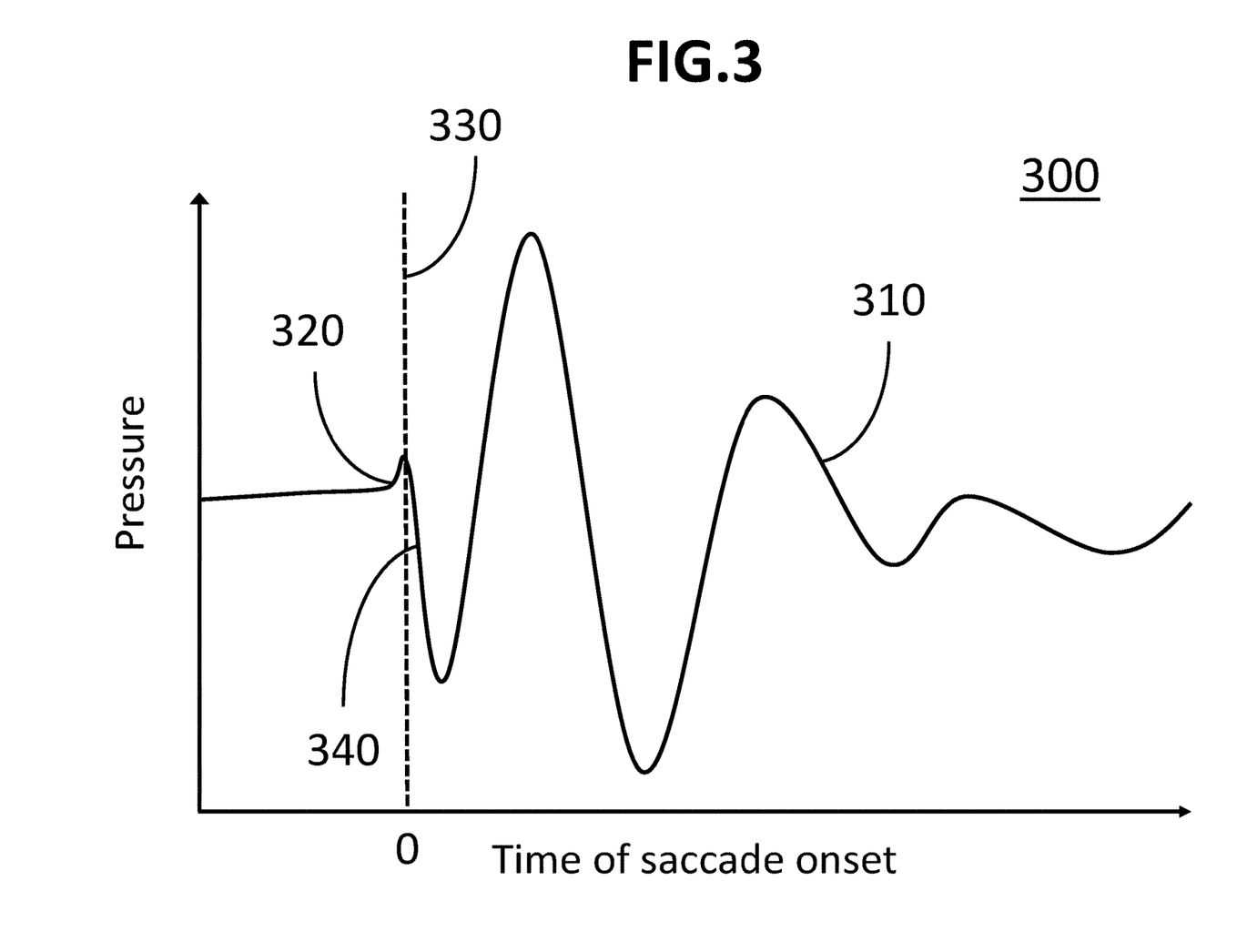
FIG. 3 is a graph illustrating changes in pressure inside a user's ear over time.

FIG. 3 is a graph 300 illustrating the particular case of changes in pressure inside a user's ear over time. Whilst FIG. 3 shows a measurement of pressure of the interior ear, any measurement that captures the movement of the ear drum, and therefore the volume of the inner ear, could be used. For example, a sonar or radar device could equally detect a change in volume of the inner ear and therefore be used to determine anticipated eye movement. It will be appreciated that a change in the volume of the interior ear of a user would be reflected in a change in pressure.

A signal 310 shows the oscillation of pressure over time. The signal 310 shows a first portion 320 having a positive deflection before the onset 330 of the eye movement. This deflection generally occurs around 10 ms before the onset 330 of the eye movement. As such, by sensing this deflection, a saccadic eye movement can be predicted before it occurs. A second portion 340 having a more substantial negative deflection occurs after the onset 330 of the eye movement. This deflection generally occurs around 5 ms after the onset 330 of the eye movement. The oscillations then continue as the saccade continues and as a new gaze point is reached.

The graph 300 is for a contralateral eye movement relative to the ear being measured. That is, the eye moves from a first gaze point towards a second gaze point further from the ear being measured. An eye movement in an ipsilateral direction (where the eye moves from a first gaze point towards a second gaze point nearer to the ear being measured) would produce a similar pattern but in the opposite sense. That is, the first portion 320 would be in a negative sense and the second portion 340 would be in a positive sense. As such, the direction of the eye movement can be determined from the sense in which the measured oscillations occur.

It has also been shown that the magnitude of the oscillations is proportional to the distance of the eye movement (often referred to as the amplitude of the saccade). As such, if a first gaze point has been determined, and a measurement of the interior ear of a user can be used to determine the direction and magnitude of an eye movement from that point, then a second gaze point can be determined. As the oscillations begin before the onset of the movement, the second gaze point can be anticipated earlier than in currently used methods.

Figure 4:
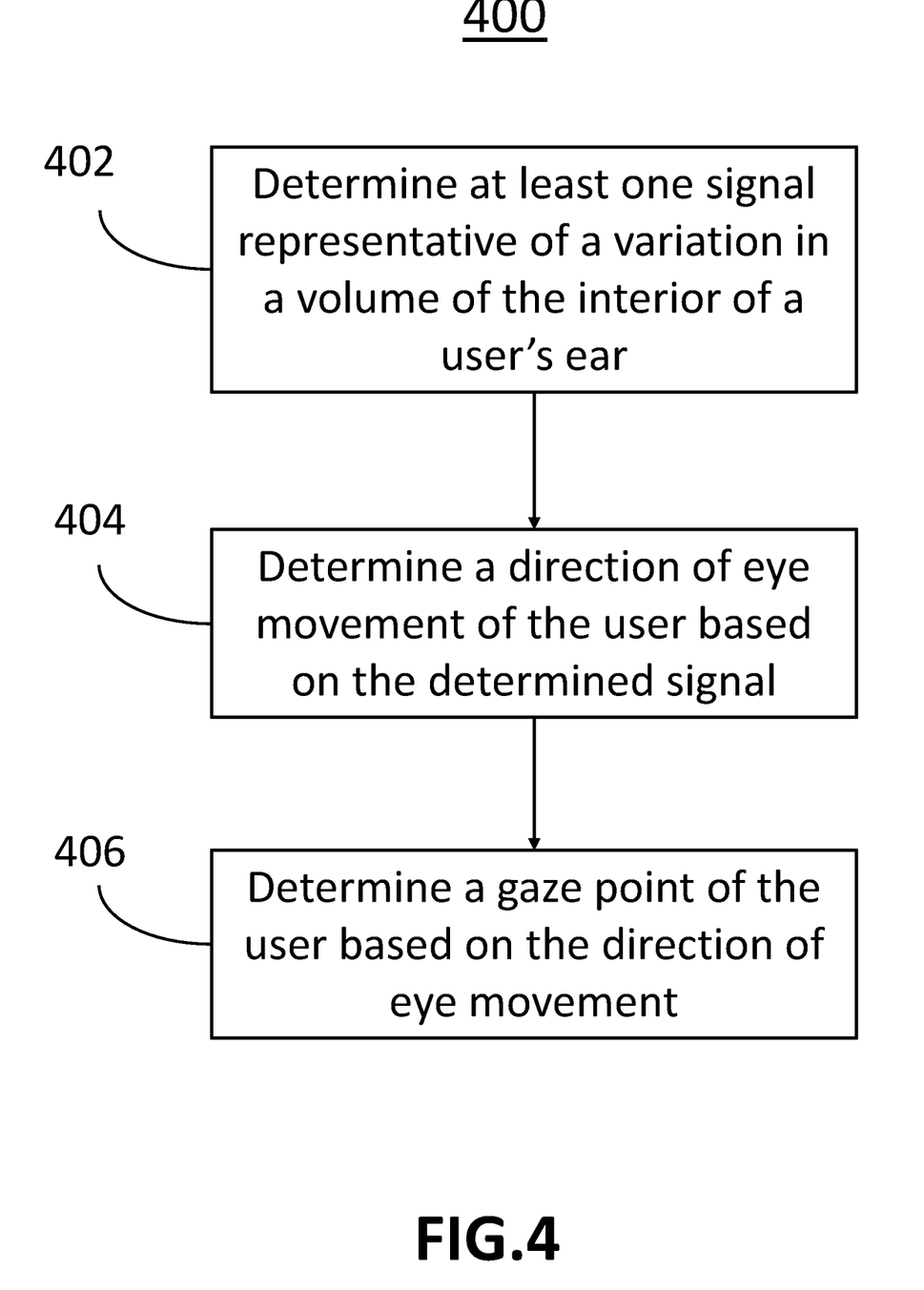
FIG. 4 is a flow chart illustrating a method of determining a gaze point of a user according to an embodiment.

FIG. 4 shows a method 400 of determining a gaze point of a user using the principles outlined above. The method may be performed by the system of FIG. 1.

At step 402, the method comprises determining at least one signal representative of a variation in a volume of the interior of a user's ear, for example the signal 310 shown in FIG. 3. The variation in a volume of the interior of a user's ear may be caused by a movement of the ear drum, as discussed above. As such, the absolute volume, of the interior of the user's ear may change. In other embodiments, the movement of the ear drum may cause a change in the shape of the interior of the user's ear without necessarily changing the absolute volume (for example, if other components of the interior of the user's ear also move). In some embodiments, the variation in the volume may be a variation in the pressure in the interior of the user's ear.

As discussed above, a sensor 150 may be used in determining the signal. In some embodiments, more than one sensor 150 may be used. The sensor 150 may be disposed inside, adjacent to or outside the user's ear, as long as it is capable of capturing changes in the volume of the interior of the user's ear. In some embodiments, the sensor 150 is a microphone. In other embodiments, the sensor 150 may be a sonar device and/or a radar device.

As discussed in relation to FIG. 3, the variation in the interior of the user's ear may begin to occur before any associated eye movement occurs. As such, the determined signal may comprise a first portion 320 corresponding to a time before the eye movement occurs. The signal may then also comprise a second portion 340 subsequent to the first portion. In some embodiments, the second portion indicates a variation in the opposite sense to the first portion. This may be indicative of an oscillation of the sensed value.

Determining the signal may be performed for both ears of the user. Whilst a signal from a single ear can be indicative of an eye movement, signals may be determined from both the left and right ear of the user. This can lead to an increase in data available to determine whether an eye movement has occurred, and can take account of cases where one ear of a user does not observe the ear drum behaviour discussed above, for example due to illness or damage.

At step 404, a direction of eye movement of the user is determined based on the determined signal, for example the direction of movement 240 shown in FIG. 2. As discussed above, movements in the interior of a user's ear can be indicative of an imminent or ongoing eye movement of the user. As such, the determined signal can be used to predict or identify movement of the user's eye.

As discussed above, a variation in volume in one sense indicates a substantially contralateral eye movement with respect to the user's ear. For example, an increase in the pressure in the left ear of the user may indicate a movement of the eye from a first gaze point towards a second gaze point to the right of the first gaze point. A variation in the volume in an opposite sense indicates a substantially ipsilateral eye movement with respect to the user's ear. For example, a decrease in the pressure in the left ear of the user may indicate a movement of the eye from a first gaze point towards a second gaze point to the left of the first gaze point.

As also discussed above, the magnitude of the variation can correspond to a magnitude of the eye movement. Therefore, based on the sensed first portion 320 of the variation, the distance of the eye movement can also be determined. This can be of further use when determining an anticipated gaze point of the user.

The first portion 320 of the variation in the interior of the user's ear may begin to occur before any associated eye movement occurs. As such, determining the direction of eye movement may be possible before the eye movement itself occurs. In this case, an anticipated gaze point can be determined based on an initial gaze point of the user and the determined direction of eye movement. This can be done by sensing the first portion 320 of the variation and determining the direction of eye movement based on the first portion 320.

The oscillation in the signal can continue while the eye movement is ongoing. In this case, instead of or in addition to detecting an anticipated gaze point, the method 400 can be used to determine a current gaze point. This can be useful where other methods of gaze detection are inaccurate, unavailable or inappropriate.

In some embodiments, the eye movement is a saccadic eye movement. That is, a rapid movement of the eye between gaze points. It has been shown that the movement of an ear drum is particularly suited to indicating horizontal movements of a user's eye. As such, the determined direction of eye movement may be substantially horizontal.

At step 406, a gaze point of the user is determined based on the direction of eye movement. This may be an anticipated gaze point, such as the anticipated gaze point 250 shown in FIG. 2. This may be determined based on an initial gaze point, for example the initial gaze point 210 shown in FIG. 2, and the determined direction of eye movement, for example the direction of movement 240. The magnitude of the detected variation can also be used to determine the distance of the eye movement (the amplitude of the saccade) and be of further use when determining an anticipated gaze point of the user. The rate of change of the gaze point of the user, also referred to as the velocity or speed of a saccade by the user, is directly dependent on the amplitude of the saccade. Thus, as the intended amplitude of a user's saccade increases, so does the speed of the saccade. Therefore, in some embodiments, the magnitude of the detected variation can be used to determine the velocity of a saccade, which can in turn be used to determine the amplitude of the saccade.

As discussed in relation to FIG. 1, eye tracking can be used to control a display device based on determined gaze points. In some embodiments, modifying the image displayed on a display device may occur in response to the detection of a change in the gaze point. This can include modifying the image at least in an area around the determined gaze point, for example the area 270 around the anticipated gaze point 250, as shown in FIG. 2. In some embodiments, the area around the initial gaze point and/or the area between gaze points may also be modified. For example, the area 220 around the initial gaze point 210 and/or the changed area 260 on the display device 110 may also be modified.

When "modification" of an image presented on the display device 110 is discussed herein, it shall be understood that what is intended is that a subsequent image displayed on the display device 110, is different than a prior image displayed on the display device 110. Thus, the graphics processing device 130 and the display device 110, or other device(s) discussed herein, "modify" an image by causing a first image to be displayed and then a second image to be displayed which is different than the first image. Any other change of an image discussed herein, for example, increasing or decreasing of image quality, shall also be understood to mean that a subsequent image is different than a prior image. Note that a change or modification of an image may include changing or modifying only a portion of the image. Thus, some portions of a prior image may be the same as a subsequent image, while other portions may be different. In other situations, the entirety of a prior image may be different than a subsequent image. It shall be understood that the modification of an area or an entirety of an image does not necessarily mean every finite portion of the area or entirety are changed (for example, each pixel), but rather that the area or entirety may be changed in some potentially consistent, predefined, or ordered manner (for example, the quality of the image is changed).

Increasing the quality of the image may include increasing the quality of any one or more of the below non-exclusive list of graphical characteristics, in addition to other possible characteristics known in the art:

Resolution: The number of distinct pixels that may be displayed in one or more dimensions. For example, "1024×768" means 1024 pixels displayed in height and 768 pixels displayed in width.

Shading: Variation of the colour and brightness of graphical objects dependent on the artificial lighting projected by light sources emulated by graphics processing device 130.

Texture-mapping: The mapping of graphical images or "textures" onto graphical objects to provide the objects with a particular look. The resolution of the textures influence the quality of the graphical object to which they are applied.

Bump-mapping: Simulation of small-scale bumps and rough gradients on surfaces of graphical objects.

Fogging/participating medium: The dimming of light when passing through non-clear atmosphere or air.

Shadows: Emulation of obstruction of light.

Soft shadows: Variance in shadowing and darkness caused by partially obscured light sources.

Reflection: Representations of mirror-like or high gloss reflective surfaces.

Transparency/opacity (optical or graphic): Sharp transmission of light through solid objects.

Translucency: Highly scattered transmission of light through solid objects.

Refraction: Bending of light associated with transparency.

Diffraction: Bending, spreading and interference of light passing by an object or aperture that disrupts the light ray.

Indirect illumination: Surfaces illuminated by light reflected off other surfaces, rather than directly from a light source (also known as global illumination).

Caustics (a form of indirect illumination): Reflection of light off a shiny object, or focusing of light through a transparent object, to produce bright highlights on another object.

Anti-aliasing: The process of blending the edge of a displayed object to reduce the appearance of sharpness or jagged lines. Typically, an algorithm is used that samples colours around the edge of the displayed object in to blend the edge to its surroundings.

Frame rate: For an animated image, the number of individual frames presented during a certain period of time to render movement within the image.

3D: Visual and temporal characteristics of an image which cause the image to appear to be three dimensional to a viewer.

The size and shape of the area of the image which may be modified to appear in greater quality can vary depending on the embodiment. Merely by way of example, the shape of the area may be circular, oval, square, rectangular, or polygonal. In some embodiments, the quality of the image within the area may be uniformly increased. In other embodiments, the increase in quality of the image may be greatest at the centre of the area (i.e., proximate to the gaze point), and decrease towards the edges of the area (i.e., distal to the gaze point), perhaps to match the quality of the image surrounding the area.

In some embodiments, the size or shape of the area around the gaze point for which an image is modified (or which remains unmodified from a heightened quality in various embodiments), is dynamic. This may occur based at least in part on any number of factors, including the current location of the gaze point relative to the image or display device. Merely by way of example, if a user moves their gaze point to a certain portion of the screen, a predefined portion of the screen may be modified via increased quality therein (for example, a corner portion of the display having a map of a virtual area in a video game). In some embodiments, if enough user saccades having one or more predefined characteristics are detected in predefined amount of time, the entirety of the display may be modified to be rendered in greater quality.

In some embodiments, an entirety of the image may be modified during the period of change in the gaze point of the user, and once the change in the gaze point of the user ceases, either the area around end gaze point of the user or a remainder of the image (portions of the image not around the end gaze point) may be modified. Merely by way of example, in one embodiment, the quality of the entire image may be increased during movement of the user's gaze (sometimes referred to as a saccade), but the increase in quality may only be sustained in an area around the user's end gaze point once the saccade is complete (i.e., the quality of the remainder of the image may be decreased upon completion of the saccade). In a different embodiment, the quality of the entire image may be decreased during a saccade, but the decrease in quality may only be sustained areas besides around the user's end gaze point once the saccade is complete (i.e., the quality of the area of the image around the user's end gaze point may be increased upon completion of the saccade).

Additionally, the use of other system resources, including for example the processor/computer 140 and related resources, may also be modified during a user's saccade. For example, non-graphical operations may be supplemented by the resources of the processor/computer 140 and the graphics processing device 130, during a saccade. More specifically, during a saccade, non-graphical calculations necessary for other system operations may proceed at greater speed or efficiency because additional resources associated with the processor/computer 140 and the graphics processing device 130 are made available for such operations.

Figure 5:
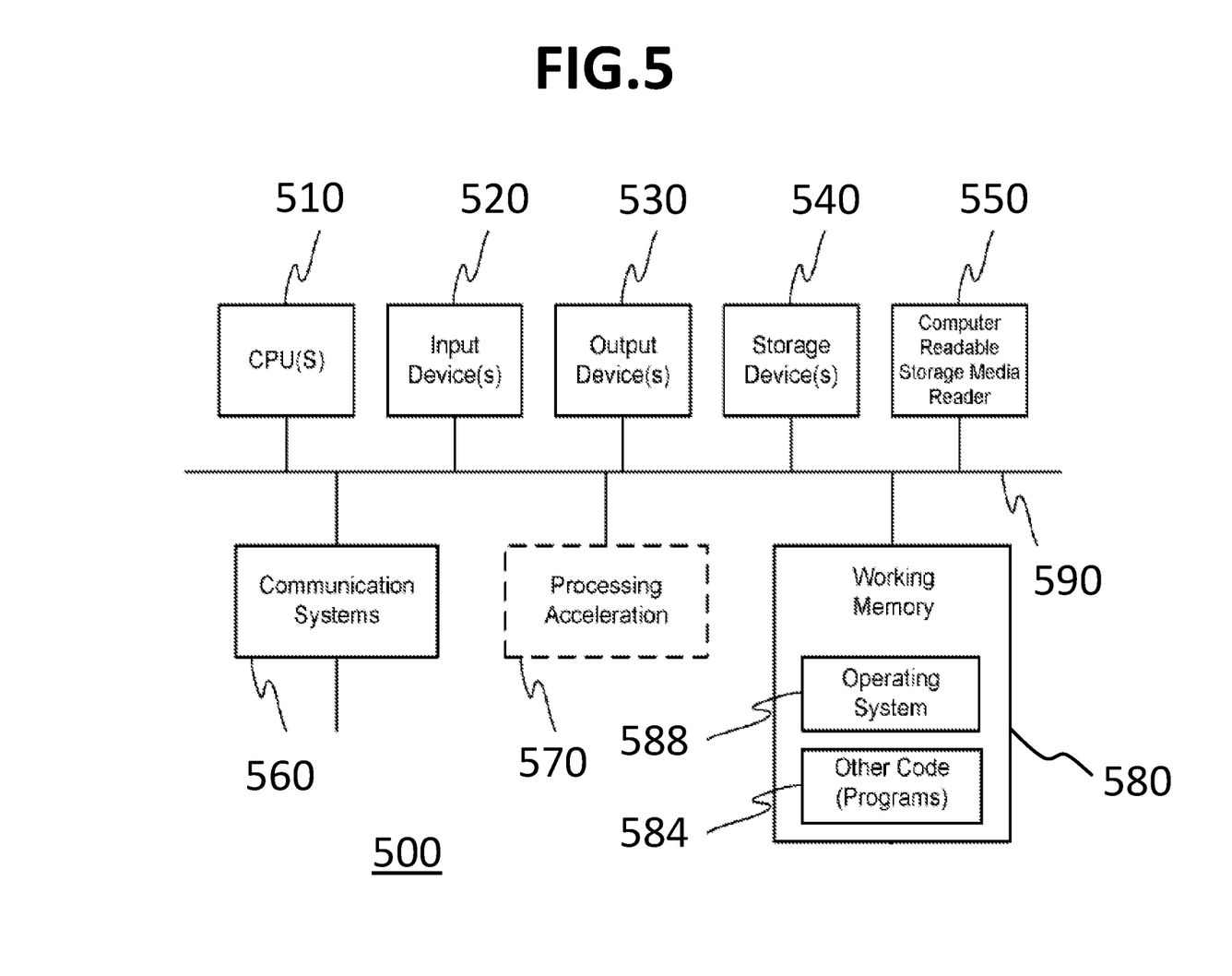
FIG. 5 is a block diagram of an exemplary computer system capable of being used in at least some portion of the devices or systems of the present invention, or implementing at least some portion of the methods of the present invention.

FIG. 5 is a block diagram illustrating an exemplary computer system 500 in which embodiments of the present invention may be implemented. This example illustrates a computer system 500 such as may be used, in whole, in part, or with various modifications, to provide the functions of the eye tracking device 120, the graphics processing device 130, the game console, the processor/computer 140, the sensor 150 and/or other components of the invention such as those discussed above. For example, various functions of the eye tracking device 120 and associated processors may be controlled by the computer system 500, including, merely by way of example, tracking a user's gaze point, determining an anticipated gaze point, controlling the graphics processing device 130, etc.

The computer system 500 is shown comprising hardware elements that may be electrically coupled via a bus 590. The hardware elements may include one or more central processing units 510, one or more input devices 520 (e.g., a mouse, a keyboard, etc.), and one or more output devices 530 (e.g., a display device, a printer, etc.). The computer system 500 may also include one or more storage device 540. By way of example, the storage device(s) 540 may be disk drives, optical storage devices, solid-state storage device such as a random-access memory ("RAM") and/or a read-only memory ("ROM"), which can be programmable, flash-updateable and/or the like.

The computer system 500 may additionally include a computer-readable storage media reader 550, a communications system 560 (e.g., a modem, a network card (wireless or wired), an infra-red communication device, Bluetooth™ device, cellular communication device, etc.), and a working memory 580, which may include RAM and ROM devices as described above. In some embodiments, the computer system 500 may also include a processing acceleration unit 570, which can include a digital signal processor, a special-purpose processor and/or the like.

The computer-readable storage media reader 550 can further be connected to a computer-readable storage medium, together (and, optionally, in combination with the storage device(s) 540) comprehensively representing remote, local, fixed, and/or removable storage devices plus storage media for temporarily and/or more permanently containing computer-readable information. The communications system 560 may permit data to be exchanged with a network, system, computer and/or other component described above.

The computer system 500 may also comprise software elements, shown as being currently located within the working memory 580, including an operating system 588 and/or other code 584. It should be appreciated that alternate embodiments of a computer system 500 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of the computer system 500 may include code 584 for implementing any or all of the function of the various elements of the architecture as described herein. For example, software, stored on and/or executed by a computer system such as the system 500, can provide the functions of the eye tracking device 120, the graphics processing device 130, the gaming console, the processor/computer 140, the sensor 150 and/or other components of the invention such as those discussed above. Methods implementable by software on some of these components have been discussed above in more detail.

The invention has now been described in detail for the purposes of clarity and understanding. However, it will be appreciated that certain changes and modifications may be practiced within the scope of the appended claims.

The invention claimed is:

1. A system for determining a gaze point of a user, the system comprising:

at least one sensor configured to determine at least one signal representative of a variation in a volume of an interior of an ear of a user; and
a display device: and
a processor configured to:
    determine a direction of eye movement of the user based on the determined signal, wherein the direction of eye movement is determined before the eye movement occurs;
    determine a gaze point of the user based on the direction of eye movement;
    determine an anticipated gaze point based on an initial gaze point of the user and the determined direction of eye movement;
    control the display device based on the determined anticipated gaze point, wherein the processor is configured to control the display device by modifying a use of at least one system resource, wherein modifying the use of the at least one system resource comprises modifying a first image displayed on the display device; and
    cause a second image to be displayed on the display device, wherein the second image is different than the first image for at least in an area around the determined anticipated gaze point, wherein the second image has increased quality compared to the first image for the area around the determined anticipated gaze point.

2. The system of claim 1, wherein the at least one sensor comprises a microphone, a sonar device and/or a radar device.

3. The system of claim 1, wherein the at least one sensor is disposed inside, adjacent to or outside the user's ear.

4. The system of claim 1, wherein the variation in a volume of the interior of a user's ear comprises a variation in a shape of the interior of the user's ear.

5. The system of claim 1, wherein the variation in a volume of the interior of a user's ear comprises a variation in a pressure in the interior of the user's ear.

6. The system of claim 1, wherein:
a variation in the volume in a first sense indicates a substantially contralateral eye movement with respect to the user's ear; and
a variation in the volume in a second sense, opposite to the first sense, indicates a substantially ipsilateral eye movement with respect to the user's ear.

7. The system of claim 1, wherein the signal comprises a first portion corresponding to a time before the eye movement occurs, and the processor is further configured to determine the direction of eye movement based on the first portion.

8. The system of claim 7, wherein each of the signal comprises a second portion subsequent to the first portion, the second portion indicating a variation in an opposite sense to the first portion.

9. The system of claim 1, wherein a magnitude of the variation corresponds to a magnitude of the eye movement.

10. The system of claim 1, wherein each of the at least one sensor comprises:
a first sensor configured to determine a first signal representative of a variation in a volume of the interior of a user's left ear; and
a second sensor configured to determine a second signal representative of a variation in a volume of the interior of a user's right ear.

11. The system of claim 1, wherein the eye movement is a saccadic eye movement.

12. The system of claim 1, wherein the direction of eye movement is substantially horizontal.

13. The system of claim 1, wherein increased quality comprises at least one selection from a group consisting of:
   increased resolution;
   increased shading quality;
   increased texture mapping quality;
   increased quality of reflection rendering;
   increased anti-aliasing;
   increased frame rate; and
   increased three-dimensional rendering quality.

14. A method of determining a gaze point of a user, the method comprising:
   determining at least one signal representative of a variation in a volume of an interior of an ear of a user;
   determining a direction of eye movement of the user based on the determined signal, wherein the direction of eye movement is determined before the eye movement occurs;
   determining a gaze point of the user based on the direction of eye movement;
   determining an anticipated gaze point based on an initial gaze point of the user and the determined direction of eye movement;
   controlling a display device based on the determined anticipated gaze point, wherein the display device is controlled by modifying a use of at least one system resource, wherein modifying the use of the at least one system resource comprises modifying a first image displayed on the display device; and
   causing a second image to be displayed on the display device, wherein the second image is different than the first image for at least in an area around the determined anticipated gaze point, wherein the second image has increased quality compared to the first image for the area around the determined anticipated gaze point.

15. A computer program product comprising a non-transitory computer-readable storage medium storing computer-executable instructions which, when executed on at least one processor, cause one or more processors to perform operations comprising:
   determining at least one signal representative of a variation in a volume of an interior of an ear of a user;
   determining a direction of eye movement of the user based on the determined signal, wherein the direction of eye movement is determined before the eye movement occurs;
   determining a gaze point of the user based on the direction of eye movement;
   determining an anticipated gaze point based on an initial gaze point of the user and the determined direction of eye movement;
   controlling a display device based on the determined anticipated gaze point, wherein the display device is controlled by modifying a use of at least one system resource, wherein modifying the use of the at least one system resource comprises modifying a first image displayed on the display device; and
   causing a second image to be displayed on the display device, wherein the second image is different than the first image for at least in an area around the determined anticipated gaze point, wherein the second image has increased quality compared to the first image for the area around the determined anticipated gaze point.

* * * * *